United States Patent
Hayashi

(10) Patent No.: US 11,801,287 B2
(45) Date of Patent: Oct. 31, 2023

(54) MATERIALS AND METHODS FOR THE DEVELOPMENT OF AN ANTIGEN-SPECIFIC IMMUNE NON-RESPONSIVENESS STATE

(71) Applicant: A & G Pharmaceutical, Inc., Columbia, MD (US)

(72) Inventor: Jun Hayashi, Columbia, MD (US)

(*) Notice: Subject to any disclaimer, the term of this patent is extended or adjusted under 35 U.S.C. 154(b) by 0 days.

(21) Appl. No.: 17/126,706

(22) Filed: Dec. 18, 2020

(65) Prior Publication Data

US 2021/0315982 A1    Oct. 14, 2021

Related U.S. Application Data

(63) Continuation of application No. 16/558,600, filed on Sep. 3, 2019, now abandoned, which is a continuation of application No. 15/231,234, filed on Aug. 8, 2016, now abandoned, which is a continuation of application No. 13/391,127, filed as application No. PCT/US2010/045753 on Aug. 17, 2010, now abandoned.

(Continued)

(51) Int. Cl.

| A61K 39/00 | (2006.01) |
|---|---|
| A61P 1/00 | (2006.01) |
| A61P 3/00 | (2006.01) |
| A61P 3/10 | (2006.01) |
| A61P 5/14 | (2006.01) |
| A61P 13/12 | (2006.01) |
| A61P 37/00 | (2006.01) |
| A61P 25/00 | (2006.01) |
| A61P 29/00 | (2006.01) |
| A61K 31/455 | (2006.01) |
| A61K 31/502 | (2006.01) |
| A61K 31/609 | (2006.01) |

(52) U.S. Cl.
CPC ........ *A61K 39/0008* (2013.01); *A61K 31/455* (2013.01); *A61K 31/502* (2013.01); *A61K 31/609* (2013.01); *A61P 1/00* (2018.01); *A61P 3/00* (2018.01); *A61P 3/10* (2018.01); *A61P 5/14* (2018.01); *A61P 13/12* (2018.01); *A61P 25/00* (2018.01); *A61P 29/00* (2018.01); *A61P 37/00* (2018.01)

(58) Field of Classification Search
CPC .. A61K 31/455; A61K 31/502; A61K 31/609; A61K 39/0008; A61P 1/00; A61P 13/12; A61P 19/02; A61P 25/00; A61P 29/00; A61P 3/00; A61P 3/10; A61P 37/00; A61P 37/06; A61P 5/14
See application file for complete search history.

(56) References Cited

FOREIGN PATENT DOCUMENTS

WO    WO-2009026239 A1 *    2/2009    ........... A61K 31/415

* cited by examiner

*Primary Examiner* — Savitha M Rao
(74) *Attorney, Agent, or Firm* — Farber LLC

(57) ABSTRACT

The present invention provides materials and methods for making a subject non-responsive to an antigen. Methods of the invention may comprise contacting the subject with the antigen and a compound that induces anergy. In some embodiments, the antigen may be an autoimmune antigen, examples of which include, but are not limited to acetylcholine receptor for myasthenia gravis, glutamic acid decarboxylase for type I diabetes mellitus and rheumatoid factor in rheumatoid arthritis. In some embodiments, the present invention provides a method of transplanting an organ, tissue, or cells into a subject (e.g. a mammal such as a human).

5 Claims, 1 Drawing Sheet

72

87

241

Related U.S. Application Data

(60) Provisional application No. 61/234,454, filed on Aug. 17, 2009.

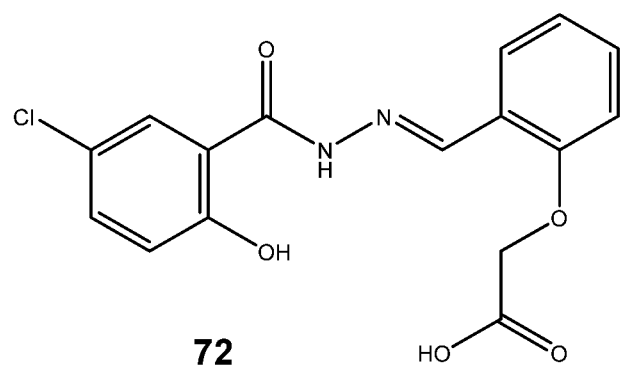
72
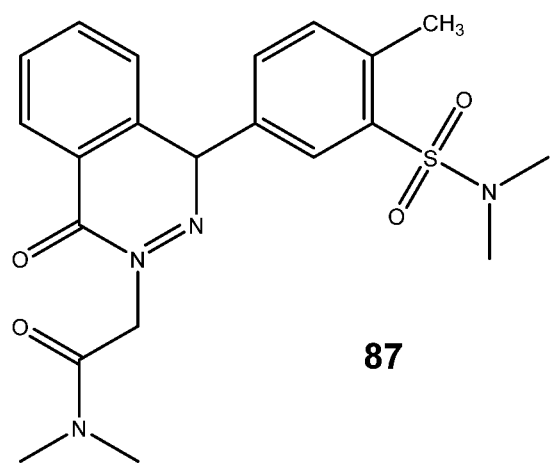
87
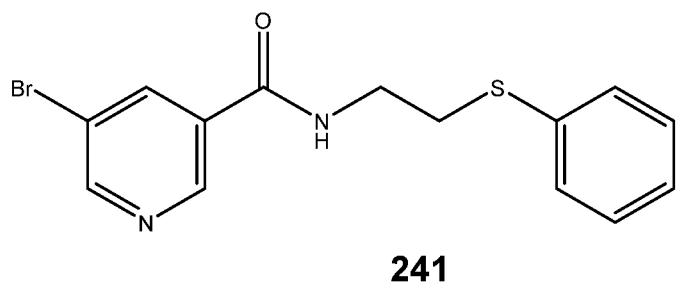
241

MATERIALS AND METHODS FOR THE DEVELOPMENT OF AN ANTIGEN-SPECIFIC IMMUNE NON-RESPONSIVENESS STATE

CROSS REFERENCE TO RELATED APPLICATIONS

This application is a continuation of U.S. application Ser. No. 16/558,600, filed Sep. 3, 2019, which is a continuation of U.S. application Ser. No. 15/231,234, filed Aug. 8, 2016, which is a continuation of U.S. application Ser. No. 13/391,127, filed May 7, 2012, now abandoned, which is the National Stage of International Application No. PCT/US2010/045753, filed Aug. 17, 2010, which claims the benefit of U.S. Provisional Application No. 61/234,454, filed Aug. 17, 2009, all of which are incorporated herein by reference in their entireties.

BACKGROUND OF THE INVENTION

The immune system recognizes self from non-self. In a healthy individual, the body's immune system is designed to mount immune response to immunogens that enter the body (non-self) but maintain non-responsiveness to the constituents of its own body (self). The immune non-responsiveness (tolerance) to self is established mainly by the elimination of self-reactive T cells (negative selection) during T cell development in the thymus. However, the elimination of self reactive T cells is not entirely dependent on negative selection. Antigen-specific immune non-responsiveness can be established by an alternative mechanism leading to a condition termed anergy.

T cells play a central role in adaptive immune response. The essential role T cells play in the immune response is well illustrated in SCID and nude mice or similar human immunodeficiency diseases where T cell component is absent or dysfunctional. T cells play an essential role in the regulation of immune response and the activation of B cells that produce antibodies. Consequently, the activation of T cells is stringently regulated. T cell activation requires the antigens to he presented by specialized antigen presenting cells (APCs). It requires the engagement of not only the antigen-recognizing receptor (T cell receptor or TCR) but also the engagement of co-receptors such as CD4 and CD28 with the corresponding ligands expressed on APCs. If T cell activation takes place in the absence of co-receptor engagement, these T cells become anergic and will not respond to the antigen, thus establishing antigen-specific immunosuppression.

The establishment of anergy is an ideal way to induce immunesuppression so that patients can establish tolerance to the antigen but will retain immunecompetence against other pathogens. Currently, all of the FDA approved immunosuppressor drugs suppress the entire immune response making patient vulnerable to infection.

The small molecule immunomodulator compounds disclosed herein target TCR proximal signaling and block APC-mediated activation of T cells by interfering with the activity of lymphocyte-specific protein tyrosine kinase (Lck). Lck is a Src family kinase that has been shown to bind with high affinity to the $\zeta$ chain ITAM-2 C terminal phosphotyrosine residues and other ITAM residues of CD3 chains. Blocking the association of Lck with the CD3 ITAM prevents T cell activation.

The present invention demonstrates that blocking Lck activity in association with the administration of antigen can induce anergy to the antigen in the T cells.

BRIEF SUMMARY OF THE INVENTION

The present invention provides materials and methods for making a subject (e.g., a mammal such as a human) non-responsive to an antigen. Methods of the invention may comprise contacting the subject with the antigen and a compound that induces anergy. Compounds that induce anergy include those that affect Lck function, Lck activity, Lck binding, Lck mediated signaling and/or Lck SH2 activity, for example, modify (increase or decrease) Lck function, Lck activity, Lck binding, Lck mediated signaling and/or Lck SH2 activity. In some embodiments, the compounds may interfere with the binding of Lck to $\zeta$ chain ITAM-2 C terminal phosphotyrosine residues and other ITAM residues of CD3 chains. In some embodiments, compounds that induce anergy may have the structure of compounds 72, 86, or 241. In some embodiments, the antigen may be an autoimmune antigen. Examples of autoimmune antigens include, but are not limited to achetylcholine receptor for myasthenia gravis, glutamic acid decarboxylase for type I diabetes mellitus and rheumatoid factor in rheumatoid arthritis.

In some embodiments, the present invention provides a method of treating an autoimmune disease in a subject (e.g., a mammal such as a human). Such methods may comprise contacting the subject with an autoimmune antigen and a compound that induces anergy. Compounds that induce anergy include those that affect Lck function, Lck activity, Lck binding, Lek mediated signaling and/or Lck SH2 activity, for example, modify (increase or decrease) Lck function, Lck activity, Lck binding, Lck mediated signaling and/or Lck SH2 activity. In some embodiments, the compounds may interfere with the binding of Lck to $\zeta$ chain ITAM-2 C terminal phosphotyrosine residues and other ITAM residues of CD3 chains. In some embodiments, compounds that induce anergy may have the structure of compounds 72, 86, or 241. Examples of autoimmune antigens include, but are not limited to achetylcholine receptor for myasthenia gravis, glutamic acid decarboxylase for type I diabetes mellitus and rheumatoid factor in rheumatoid arthritis. Autoimmune diseases that may be treated include, but are not limited to, rheumatoid arthritis, glomerulonephritis, Hashimoto's thyroiditis, multiple sclerosis, systemic lupus erythematosus, myasthenia gravis, autoimmune hemolytic anemia, autoimmune thrombocytopenic purpura, type 1 diabetes, Chrohn's disease, Grave's disease, celiac disease, and the like.

In some embodiments, the present invention provides a method of transplanting an organ, tissue, or cells into a subject (e.g., a mammal such as a human). Such methods may comprise surgically implanting the organ in the subject and administering a compound that induces anergy. Any organ may be transplanted using the methods of the invention, for example, heart, lung, liver, and kidney. Compounds that induce anergy include those that affect Lek function, Lck activity, Lck binding, Lck mediated signaling and/or Lck SH2 activity, for example, modify (increase or decrease) Lck function, Lck activity, Lck binding, Lck mediated signaling and/or Lck SH2 activity. In some embodiments, the compounds may interfere with the binding of Lck to $\zeta$ chain ITAM-2 C terminal phosphotyrosine residues and other ITAM residues of CD3 chains. In some embodiments, compounds that induce anergy may have the structure of compounds 72, 86, or 241.

BRIEF DESCRIPTION OF THE DRAWINGS

FIG. 1 shows the chemical structures of the compounds of the invention.

DETAILED DESCRIPTION OF THE INVENTION

The compounds of the invention are shown in FIG. 1. The present invention encompasses various modifications of the compounds as disclosed herein, such as pharmaceutically acceptable salts and prodrugs of all the compounds of the present invention. Preferably, the salts formed are pharmaceutically acceptable for administration to mammals, for example, humans.

The compounds of the invention can be administered alone or as an ingredient, for example, an active ingredient, in a composition such as a formulation. Thus, the present invention also includes pharmaceutical compositions of a compound of the invention or a salt thereof, containing, for example, one or more pharmaceutically acceptable carriers.

Typically, compounds of the invention will be administered in combination with an antigen or antigens to which anergy is to be induced. Compounds of the invention may be administered before, simultaneously with, and/or after administration of the antigen. In one embodiment, the antigen will be administered and one or more compounds of the invention will be administered after the antigen. Optionally, compounds of the invention may be administered multiple times, for example, before, simultaneously with, and/or after administration of the antigen. Antigen may be administered in any suitable amount, for example, from about 0.1 mg/kg body weight to about 100 mg/kg body weight.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Isol, editor), 1553-1593 (current edition).

Compounds and compositions of the invention may be administered in a suitable fashion known to those skilled in the art. For example, they may be administered orally, nasally, parenterally (subcutaneously, intravenously, intramuscularly, intrasternally, and by infusion) by inhalation, rectally, vaginally, topically and by ocular administration. Injection can be, e.g., intramuscular, intraperitoneal, intravenous, etc.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art including, but not limited, to suspending agents, solubilizers, buffering agents, binders, disintegrants, preservatives, colorants, flavorants, lubricants and the like. Time-release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made.

The compounds can be administered as the sole active agent or in combination with other pharmaceutical agents, such as other agents which inhibit or stimulate tyrosine kinases, signal transduction processes, cell proliferation and/or immune responses. Inhibitory agents include, e.g., cyclosporine and FK506, rapamycin, leflunomide, butenamindes, corticosteroids, atomeric acid, dipeptide derivative, tyrphostin or the like. In such combinations, each active ingredient can be administered either in accordance with its usual dosage range or a dose below its usual dosage range. Doses may be administered simultaneously or sequentially with either compounds of the invention being administered before or after the other pharmaceutical agent.

The dosages of the compounds of the present invention depend upon a variety of factors including the particular syndrome to be treated, the severity of the symptoms, the age, sex and physical condition of the patient, the route of administration, the frequency of the dosage interval, the particular compound utilized, the efficacy, toxicology profile, pharmacokinetic profile of the compound, and the presence of any deleterious side-effects, among other considerations.

Typically, compounds of the invention will be administered in an effective amount. An "effective amount," in reference to the methods of the invention, for example, methods of methods for making a subject (e.g., a mammal such as a human) non-responsive to an antigen, methods of treating an autoimmune disease in a subject (e.g., a mammal such as a human), and/or methods of transplanting an organ into a subject (e.g., a mammal such as a human), is an amount sufficient for preventing, slowing the onset of, ameliorating and/or reducing an unwanted immune response.

The compounds of the invention are administered at dosage levels and in a manner customary for Lck kinase inhibitors or stimulators, or other analogous drugs, such as those mentioned above. For example, cyclosporine is administered (for transplants) at about 7.95±2.81 mg/kg/day (see PDR (Physician's Desk Reference)); FK506 is administered (for transplants) at about 0.15-0.30 mg/kg/day (see PDR); and rapamycin is administered (for transplants) at about 2-6 mg/day, e.g., about 0.024 mg/kg/day for an 81 kg adult (see Thomas A. Stargy Transplantation Institute web site). See also, e.g., disclosures in U.S. Pat. Nos. 5,688,824, 5,914,343, 5,217,999, 6,133,301 and publications cited therein.

Compounds of the invention or a salt thereof, can be administered, in single or multiple doses, at a dosage level of, for example, 1 µg/kg to 500 mg/kg of body weight of patient/day, preferably between about 100 µg/kg/day and 25 mg/kg/day. Dosages can be adjusted so as to generate anergy, as desired. A lower dosage can be between about 1 pg/kg/day and 750 µg/kg/day, preferably between about 10 µg/kg/day and 500 mg/kg/day. A higher dosage can be between about 1 mg/kg/day and 750 mg/kg/day, preferably between about 10 mg/kg/day and 450 mg/kg/day.

In some embodiments, the invention includes methods of treating subjects suffering from autoimmune disorders, such as, e.g., rheumatoid arthritis, glomerulonephritis, Hashimoto's thyroiditis, multiple sclerosis, systemic lupus erythematosus, myasthenia gravis, autoimmune hemolytic anemia, autoimmune thrombocytopenic purpura, type 1 diabetes, Chrohn's disease, Grave's disease, celiac disease, or the like, with a compound of the invention in combination with an autoimmune antigen. Compounds of the invention are also useful for treating tissue or organ transplant rejection, e.g., hyper-acute or chronic graft-vs-host disease, allograft or xenograft rejection, etc by administering the compounds prior to, simultaneously with and/or after transplanting the tissue or organ.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Experimental System
Popliteal Lymph Node Assay (PLNA):

PLNA is a quantitative in vivo local graft vs host (GvH) allogeneic reaction that measures T cell activation. A mouse of a first strain (Strain A) is injected in the foot pad with lymphocytes from a mouse of a second stain (strain B). The injected lymphocytes from Stain B will cause a local GvH reaction in the popliteal lymph node of the first mouse (Stain A) causing swelling of the node due to the activation and proliferation of allogeneic T cells. The increase in mass of the popliteal lymph nodes can be measured by weighing the isolated node.

PLNA takes 1 week where at day 0, $1.5 \times 10^6$ lymph node lymphocytes from strain B mice are injected to the foot pad of strain A mice. Mice are sacrificed on day 7 and popliteal lymph nodes are removed and weighed. Typically, two to three-fold increase in the weight of popliteal lymph node can be observed in this GvH reaction. The immunosuppressive effect of compounds of interest can be studied using PLNA by measuring the suppression of popliteal lymph node weight increase compared to the control. Compounds arc injected i.p. (1 mg/Kg body weight) on days 0, 1, 2, 3, and 4. Control mice receive vehicle only.

Example 2

Assessment of Anergy Induction by Compounds Using PLNA.

In order to test the induction of anergy by the compounds, strain A mice can be re-challenged by strain B lymphocytes on day 7. Popliteal lymph nodes are harvested on day 14 and weighed. In the absence of anergy, popliteal lymph node remains swollen due to the re-challenge. If anergy is established by the compound in strain A mice against strain B lymphocytes, popliteal lymph node swelling in strain A mice will be suppressed upon strain B lymphocyte re-challenge, however, popliteal lymph node swelling should be observed if the strain A mice anergic to strain B lymphocytes are re-challenged by lymphocytes from strain C (FIG. 1A).

Experimental Design.

Out bred Swiss Webster mice were used as recipient. Lymphocytes from FVB mice were used for PLNA. For assessment of anergy induction by the compounds, Swiss mice were re-challenged using lymphocytes from FVB and SJL mice (FIG. 1B).

Blank control received PBS injection in footpad on days 0 and 7 with i.p. injection of vehicle for 4 days. Mice were sacrificed on day 14 (n=3).

Positive control received FVB lymphocytes ($1.5 \times 10^6$ cells) injections in footpad on day 0 and 7 with i.p. injection of vehicle for 4 days. Mice were sacrificed and popliteal lymph node harvested on day 14 (n=3).

Anergy experiment: Swiss mice received FVB lymphocyte ($1.5 \times 10^6$ cells) injections in footpad on day 0 in PBS. Compounds were dissolved in DMSO at 1000× concentration and 0.1% vol/vol was added to olive oil. Compounds (1 mg/Kg body weight) were injected i.p. on days 0, 1, 2, 3, and 4. Mice were re-challenged by FVB lymphocytes ($1.5 \times 10^6$ cells) injections in footpad on day 7. Mice were sacrificed and popliteal lymph node harvested on day 14 (n=3).

Anergy experiment control: Swiss mice received FVB lymphocytes ($1.5 \times 10^6$ cells) injections in footpad on days 0. Compounds (1 mg/Kg body weight) were injected i.p. on days 0, 1, 2, 3, and 4. Mice were re-challenged by SJL lymphocytes ($1.5 \times 10^6$ cells) on day 7. Mice were sacrificed and popliteal lymph node harvested on day 14 (n=3).

Mice were sacrificed on day 14 and popliteal lymph nodes were removed and weighed. As shown in Table 1, the weights of lymph nodes from the blank control animals were 1.85±0.3 mg. Lymph nodes from positive controls weighed 4.3 E 0.56 mg for FVB lymphocytes and 4.98±0.89 mg for SJL lymphocytes injected mice respectively. In FVB lymphocyte injected, compound treated mice, the increase in lymph node swelling upon re-challenge with FVB lymphocytes did not take place. However, lymph node swelling was observed in these mice when they were re-challenged with SJL lymphocytes clearly indicating the establishment of anergy (Table 1). It is clear from our positive controls that FVB lymphocyte injection induces GyH reaction and lymph node swelling in the absence of compounds.

These results indicate that the tested compounds can block T cell activation in a antigen specific manner and induce anergy to T cells when mice are challenged with T cell antigen.

TABLE 1

| Induction of anergy by compounds | | |
|---|---|---|
| Treatment | | Lymph node weight (mg) |
| Controls[§1] | PBS | 1.86 ± 0.31 |
| | FVB Lymphocytes | 4.30 ± 0.56 |
| | SJL Lymphocytes | 4.98 ± 0.89 |
| Compound 72[§2] | PBS | 3.00 ± 0.78 |
| | FVB Lymphocytes | 2.73 ± 0.68* |
| | SJL Lymphocytes | 5.74 ± 1.71 |
| Compound 86[§2] | PBS | 2.17 ± 0.31 |
| | FVB Lymphocytes | 2.20 ± 0.50* |
| | SJL Lymphocytes | 4.34 ± 1.09 |
| Compound 241[§2] | PBS | 1.95 ± 0.34 |
| | FVB Lymphocytes | 2.42 ± 0.78* |
| | SJL Lymphocytes | 5.61 ± 0.99 |

*$P < 0.001$ over SJL lymphocyte-mediated stimulation. No significant difference between FVB lymphocyte re-challenged group and PBS controls in compound treated groups. (one tailed student t test).

[§1] Swiss mice were injected with lymphocytes ($1.5 \times 10^6$ cells) from FBV or SJL mice on day 0 and popliteal lymph nodes collected on day 7 as positive controls. PBS served as negative control.

[§2] Swiss mice were injected with lymphocytes ($1.5 \times 10^6$ cells) from FBV mice on day 0. The indicated compound was injected on days 0, 1, 2, 3, and 4. On day 7, mice were re-challenged with lymphocytes ($1.5 \times 10^6$ cells) from indicated mouse strain. On day 14, mice were terminated and popliteal lymph nodes isolated and weighed.

While the foregoing invention has been described in some detail for purposes of clarity and understanding, it will be appreciated by one skilled in the art from a reading of this disclosure that various changes in form and detail can be made without departing from the true scope of the invention and appended claims. All patents and publications cited herein are entirely incorporated herein by reference.

What is claimed is:

1. A method of making a subject non-responsive to an antigen, comprising: administering the antigen to the subject; and administering an effective amount of a compound to the subject; the compound being selected from the group consisting of:

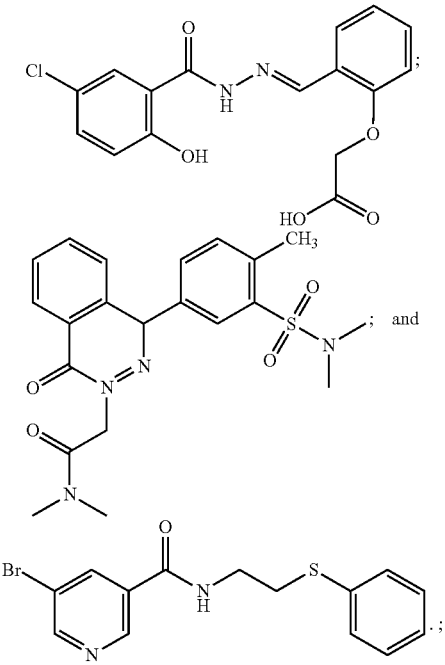

wherein the compound prevents T cell activation by interfering with the binding of lymphocyte-specific protein tyrosine kinase (Lck) in the T cell to ITAM-2 ζ chain C terminal phosphotyrosine residues.

2. The method of claim 1, wherein the effective amount of the compound is administered before, simultaneously with, and/or after administration of the antigen.

3. The method of claim 1, wherein the antigen is an autoimmune antigen selected from acetylcholine receptor for myasthenia gravis, glutamic acid decarboxylase for type I diabetes mellitus and rheumatoid factor in rheumatoid arthritis.

4. The method of claim 1, wherein the effective amount is from about 0.1 mg/kg body weight to about 100 mg/kg body weight.

5. The method of claim 1, wherein the effective amount is 1 mg/kg body weight.

* * * * *